United States Patent [19]

Luedders et al.

[11] 4,045,548

[45] Aug. 30, 1977

[54] AEROSOL ANTIPERSPIRANT CONTAINING EMOLLIENTS

[75] Inventors: Wilmer Louis Luedders, Cincinnati; Thomas Andrew Wetzel, Green Township, Hamilton County, both of Ohio

[73] Assignee: The Procter & Gamble Company, Cincinnati, Ohio

[21] Appl. No.: 571,812

[22] Filed: Apr. 25, 1975

Related U.S. Application Data

[63] Continuation of Ser. No. 442,299, Feb. 13, 1974, abandoned, which is a continuation of Ser. No. 190,303, Oct. 18, 1971, abandoned, which is a continuation-in-part of Ser. No. 59,694, July 30, 1970, abandoned.

[51] Int. Cl.$^2$ .......................... A61K 7/34; A61K 7/36; A61K 7/38
[52] U.S. Cl. ........................................................ 424/47
[58] Field of Search .................................... 424/46, 47

[56] References Cited

U.S. PATENT DOCUMENTS

| 2,906,668 | /1959 | Beekman | 424/66 |
|---|---|---|---|
| 2,957,838 | 10/1960 | Mills, Jr. | 424/47 |
| 3,088,874 | 5/1963 | Geary et al. | 424/47 |
| 3,288,681 | /1966 | Goldberg et al. | 424/47 X |
| 3,544,258 | 12/1970 | Presant et al. | 424/47 X |
| 3,579,629 | 5/1971 | Pasero et al. | 424/47 |
| Re. 26,250 | 8/1967 | Grant | 424/68 X |

FOREIGN PATENT DOCUMENTS

| 1,026,831 | 4/1966 | United Kingdom | 424/45 |

OTHER PUBLICATIONS

International Encyclopedia of Cosmetic Material, Trade Names, pp. 11, 40, 77, 122, 286, & 323.

*Primary Examiner*—Dale R. Ore
*Attorney, Agent, or Firm*—Ronald H. Kullick; George W. Allen; John A. O'Toole

[57] ABSTRACT

Organic compounds containing multiple ester groups are used in dry powder aerosol antiperspirant compositions to give greater antiperspirant effectiveness and act as a carrier for powder aluminum chlorhydroxide particles to the skin and to prevent clogging. The preferred esters are characterized by having from 12 to 16 carbon atoms and a ratio of ester groups to the number of carbon atoms of from about 0.125 to about 0.214. Diisopropyl adipate is most preferred.

8 Claims, No Drawings

AEROSOL ANTIPERSPIRANT CONTAINING EMOLLIENTS

CROSS-REFERENCE TO RELATED APPLICATION

This application is a continuation application of application Ser. No. 442,299 filed Feb. 13, 1974, now abandoned, which is a continuation application of application Ser. No. 190,303, filed Oct. 18, 1971, now abandoned, which, in turn, was a continuation-in-part application Ser. No. 59,694, filed July 30, 1970, and now abandoned.

BACKGROUND OF THE INVENTION

1. Field of the Invention

Antiperspirant compositions have been known in the art for many years and are available in several forms. Examples of said compositions are aqueous lotions, creams and sticks. Recent developments have seen the emergence of aerosols under pressure which have become a very prominent means of application to the skin. Most recently, it has become especially preferred to suspend the antiperspirant active compound as a dry, impalpable powder in a non-aqueous liquefied propellant form. Application to the skin in such a form is cosmetically desirable in that effective antiperspirant salts can be conveniently applied to the skin and feel smooth, dry and comfortable. Furthermore, such dry formulations are commercially desirable in that since the antiperspirant compound is not dissolved in a liquid medium, it is not corrosive to ordinary metal aerosol cans; and it is, therefore, not necessary to use especially lined cans or unbreakable glass bottles, both of which are expensive.

A typical dry aerosol antiperspirant composition generally contains the following ingredients: one or more metallic acid astringent salts as the antiperspirant active compound; a suspending agent employed to keep the antiperspirant compound from agglomerating or settling out and packing tightly at the bottom of the aerosol container; an emollient carrier liquid for the purpose of carrying the antiperspirant active from the aerosol container to the skin such that the the antiperspirant adheres to the skin in the form of a moist spray rather than a dusty cloud. The carrier is also important in that it acts as a means to keep the nozzle free for subsequent usage. A propellant is also employed for the purpose of expelling the above components from the desired container. In addition, minor adjuncts are optional, such as antimicrobial compounds and perfumes.

2. Prior Art

Various dry aerosol antiperspirant compositions utilizing a variety of carrier liquids have been disclosed in the patent literature. For example, Netherlands Patent 6613/943 granted to Spitzer et al on Apr. 4, 1968; U.S. Pat. No. 3,288,681 granted to Goldberg et al on Nov. 29, 1966; British Pat. No. 987,301 granted to Shulton Inc. on Mar. 24, 1965; and U.S. Pat. No. 26,250 granted Aug. 15, 1967 which was originally U.S. Pat. No. 3,030,274 granted on Apr. 17, 1962 to Grant.

SUMMARY OF THE INVENTION

It has been surprisingly found that certain organic compounds containing multiple ester groups possess characteristics that are highly desirable for an emollient-carrier and significantly increase the antiperspirant effectiveness when used in powder aerosol antiperspirant compositions which consist essentially of:

A. From about 1% to about 12% by weight of a finely divided powder antiperspirant compound comprising an acidic, metallic salt that is insoluble in the composition;
B. from about 0.1% to about 1.0% by weight of a suspending agent for the antiperspirant powder;
C. From about 1.0% to about 15.0% by weight of a hydrophobic emollient-carrier liquid comprising an organic acid having multiple ester groups, the ratio of ester groups to carbon atoms being from about 0.125 to about 0.214, said emollient-carrier liquid having a solubility in water of from about 0.0005% to about 0.1% at 30° C.; and
D. An anhydrous, non-toxic liquefiable propellant gas under pressure in an amount sufficient to produce an aerosol spray.

In addition to the above components, it is to be recognized that optional ingredients which further enhance the desirability of the antiperspirant compositions may be employed.

DETAILED DESCRIPTION OF THE INVENTION

Components of the Antiperspirant Formulation

Component A — Suitable antiperspirant compounds for use in this invention can be any of those well known in the art that are insoluble in the aerosol composition as a whole. Generally, these are acidic, metallic salts, often of aluminum, zirconium or zinc. Most preferably, aluminum chlorhydroxide (ACH) is used, although other astringent salts are also suitable. Examples of other salts are aluminum chloride, aluminum sulfate, aluminum oxychloride, aluminum oxyfulfate zirconyl hydroxychloride, zirconium oxychloride, zinc sulfate and zinc sulfocarbolate. Many inorganic-organic mixtures and complexes are also known in addition to the simple antiperspirant salts. Examples of these are zirconium salt/amine/and amino acid complexes as taught by Siegal in U.S. Pat. No. 3,407,254 (Oct. 22, 1968); e.g., complexes of the formula:

in which:
1. R is a nucleophilic compound,
2. R' is an amino acid compound,
3. n is a number of from 1 to 32 inclusive, and corresponds to the number of zirconium atoms in the molecules of the complex,
4. a is a number of from 1 to 5 inclusive,
5. b is a number of from 1 to 5 inclusive,
6. c is a number from 0 to 4 inclusive,
7. a+b+c has a value of from 2 to 6 inclusive, and
8. wherein R, R', H₂O and O, when present, are attached directly to Zr;

zirconium salt/aluminum chlorhydroxide/glycol complexes as taught by Jones et al. in U.S. Pat. No. 3,405,153 (Oct. 8, 1968), e.g., inorganic-organic complexes having the formula:

wherein Q is a member of the group consisting of zinc chloride zinc iodide, zinc bromide, zinc hydroxy chloride, zinc hydroxy iodide, zinc hydroxy bromide, zirconyl chloride, and zirconyl hydroxy chloride; A is an anion selected from the group consisting of chloride, bromide and iodide; R" is the coordinating moiety of a polyhydroxy compound having at least two carbon atoms to which are attached at least two hydroxy groups, and n' is the number of moles of Q and is at least 0.05; aluminum chlorhydroxide/glycol complexes as taught by Jones et al. in U.S. Pat. No. 3,420,932 (Jan. 7, 1969), e.g., complexes having the formula:

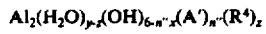

wherein A' is selected from the class consisting of chloride, bromide, iodide, sulfate and sulfamate; R$^4$ is the coordinating moiety of a polyhydroxy compound having a carbon chain in which at least two carbon atoms link a hydroxyl group to said chain, n" is a positive integer of from 1 to 4; x is the valence of A', y is a value of about 0.5 to 6 and is always such that (y−z) does not give a negative value; and z is the number of available coordinating sites, with n"x being from 2 to 4; zirconyl and aluminum halohydroxy complexes as taught by Beekman in U.S. Pat. No. 2,906,668 (Sept. 29, 1959), e.g., complexes having the formula:

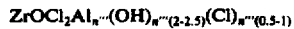

in which n''' is a number within the range 2–10 and the numbers of OH groups and Cl atoms are so selected, within the ranges stated, that their total will be 3n''': aluminum-zirconium complexes as disclosed in the copending application of Raymond E. Bolich, Jr., Ser. No. 59,690 filed July 30, 1970 entitled "ALUMINUM-ZIRCONIUM AEROSOL ANTIPERSPIRANT COMPOSITION AND PROCESS", e.g., a complex prepared by:

A. Heating an aqueous solution containing from about 1 to about 3.2 parts of aluminum chlorhydroxide to a temperature of about 190° F. to about 225° F.;

B. Adding an aqueous solution containing 1 part zirconyl hydroxychloride ratewise to the aluminum chlorhydroxide solution over a period of from about 2 hours to about 5 hours while heating and agitating, the total solids content at this point being at least about 10%; and C. Heating and agitating the aluminum chlorhydroxidezirconyl hydroxychloride mixture at a temperature of from about 190° F. to about 225° F. for from about ½ hour to about 5 hours until a stable complex forms; and aluminum and zirconium hydroxychloride complexes as disclosed in U.S. Pat. No. 3,792,068, Feb. 12, 1974, to William L. Luedders et al., entitled "DRY POWDER AEROSOL ANTIPERSPIRANT COMPOSITION INCORPORATING DRY POWDER ANTIPERSPIRANT ACTIVE COMPLEX AND PROCESS FOR ITS PREPARATION," e.g., complexes prepared by:

A. Co-dissolving in water
1. one part Al$_2$(OH)$_{6-m}$X$_m$, wherein X is an anion selected from the group consisting of choride, bromide and iodide and m is an integer from about 0.8 to about 1.2;
2. n$^4$ parts ZrY wherein Y is an anion selected from the group consisting of —O(OH)Cl and OCl$_2$, and where n$^4$ has a value of from about 0.16 to about 1.2;
3. p parts neutral amino acid selected from the group consisting of glycine, dl-tryptophane, dl-β-phenylalanine, dl-valine, dl-methionine and β-alanine, and where p has a value of from about 0.06 to about 0.53;

B. Co-drying the resultant mixture at a temperature of from about 100° C. to about 230° C. to a moisture level of from about 0.5% to about 15% by weight; and C. Comminuting the resultant dried inorganic-organic antiperspirant complex into the form of an impalpable powder.

These patents and applications are incorporated herein by reference.

Commercial availablity of the above antiperspirant salts is wide spread, and the choice of the desired antiperspirant compound is limited only by factors well known to those skilled in the art. Aluminum chlorhydroxide and complexes of aluminum chlorhydroxide and zirconyl hydroxy chloride are most preferred purposes of the present invention.

In dry aerosol antiperspirant compositions, the antiperspirant active is dispersed as a finely divided powder. The powder must be in the form of a uniform size particle and must be small enough to pass through the valve of an aerosol container without clogging. The particle size must also be such that the antiperspirant is adequately dispersed on the skin and reacts rapidly enough with the moisture of the skin and air to convert the antiperspirant compound from a dry powder into a solution which is needed for effectiveness in suppressing perspiration. In this connection, the emollient-carrier of the present invention which will be discussed in more detail hereinafter is also a very important part of this mechanism.

Particle sizes smaller than about 100 microns have been found to be suitable for the practice of the present invention, with particles averaging in size of from about 10 microns to about 25 microns being preferred. Normally, a concentration of antiperspirant salts of from about 1% to about 12% by weight of the composition is a desirable amount for perspiration control. Below about 1%, the antiperspirant effectiveness drops off, while above about 12%, is not practical because the viscosity of the product increases so that handling is more difficult and atomization is less satisfactory. The most preferred range is from about 2.5% to about 6%.

Component (B) — Suitable suspending agents can be selected from a wide number of commercially available compounds. Examples of such suspending agents include hydrophobic treated clays that swell in organic solvents, an example of which is hydrophobic bentonite, e.g., Bentone 38 (Bentone is a trademark), colloidal silicas, for example, Cab-O-Sil M-5 (Trademark) as taught by Spitzer in Netherlands application 66/13943 (Apr. 4, 1968), a submicroscopic particulate silica prepared in a hot gas environment (1100° C.) by the vapor phase hydrolysis of a silicon compound; and grease foaming soaps such as aluminum stearate. Another desirable suspending agent for purposes of the present invention is a saturated aliphatic monoalkylol amide of from about 12 to about 20 carbon atoms in the fatty acid chain and 2 or 3 carbon atoms in the alkylol chain, as disclosed by Danneman et al. in their copending U.S. application Ser. No. 888,958 filed Dec. 29, 1969. Examples include coconut monoethanol amide, octadecyl monoethanol amide and stearoyl monoethanol amide. Still another desirable suspending agent is a primary aliphatic amine of from about 12 to about 20 carbon atoms in length, as disclosed by Scripps et al. in their copending U.S. application Ser. No. 888,959 filed Dec. 29, 1969. Examples are lauryl amine, stearyl amine, tetradecyl amine, hexadecyl amine, octadecyl amine and eicosyl amine. Agents of the aforedescribed type are of colloidal dimensions and in general have a particle size of below 0.03 microns. In general, these agents are present in the compositions of the present invention in amounts of from about 0.1% to about 1.0% by weight of the total composition, and preferably, from about 0.3% to about 0.8% by weight. Such agents are valuable in keeping the aforementioned finely divided powdered antiperspirant compound suspended in the composition as a whole. The antiperspirant does not settle to the bottom of the aerosol container, and pack tightly into a compact solid mass, nor does it clump or coagulate into large agglomerates that cannot be dispersed and dispensed with substantial uniformity.

Component (C) — The newly discovered emollient-carrier agent of the present invention is an organic ester of from about 12 to about 16 carbon atoms in length wherein the ratio of the number of ester groups to carbons is from about 0.125 to about 0.214. A ratio of from about 0.167 to about 0.214 is especially preferred. The compounds of the present invention are further characterized as being non-volatile, hydrophobic liquids. The compounds of the present invention have a solubility in water of from about 0.0005% to about 0.1%, preferably from about 0.001% to about 0.02% at 30° C. Without intending to be bound by theory, it is suggested that the compounds of the present invention act in a manner such that the powder antiperspirant salt becomes more readily soluble thereby significantly increasing antiperspirant effectiveness. In addition to significantly increasing the antiperspirant protection, said emollient-carrier compounds also impart a highly desirable cosmetic feeling to the skin when applied thereto, and reduce the likelihood of breathing the otherwise dry powder. Said compound also aids efficacy by keeping the antiperspirant compound in contact with the skin so that it does not flake or wash off.

From about 1% to about 15% by weight of the compounds of the present invention are suitable for the practice of the instant invention. Amounts of from about 6% to about 10% are especially preferred. Below about 1% the emollient-carrier liquid is insufficient to form a moist spray and the spray is, therefore, undesirably dusty and gritty and does not adhere well to the skin. In addition, the increased antiperspirant effectiveness is also diminished. Above about 15%, the composition deposited upon the skin feels undesirably oily and greasy.

Preferred emollient-carrier compounds of the present invention are di-n-butyl phthalate, diethyl sebacate, diethyl sebacate, diisopropyl adipate and ethyl ethyl carbomethyl phthalate [ortho $C_2H_5OOC$-$\phi$-$COOCH_2$-$COOC_2H_5$]. Diisopropyl adipate is most preferred.

The compounds of the present invention are readily commercially available and can be synthesized by known laboratory procedures.

Component (D) — The propellant gas of the instant invention can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, propane, butane, 1,1-difluoroethane, 1,1-difluoro-1-chloroethane, dichloromonofluoromethane, methylene chloride, and isobutane, used singly or admixed. Trichlorofluoromethane, dichlorodifluoromethane, dichloroetetfluoroethane, and isobutane, used singly or admixed, are preferred.

Selection of appropriate amounts of the propellant gas is governed by normal factors as well known in the aerosol art. Generally, it is satisfactory to consider the propellant as constituting the balance of the composition of the instant invention that is not accounted for by the other components disclosed heretofore and hereinafter. Generally, the propellants make up from about 70.7% to about 93.9% of the composition by weight. Especially preferred limits are from about 80% to about 92%.

Components (E) & (F) — In addition to the essential ingredients heretofore discussed, minor ingredients are commonly used and are optional. An example of such an ingredient is an antimicrobial compound such as hexachlorophene, trichlorocarbanilide, trifluoromethylcarbanilide, tribromosalicylanide and 2,4,4'- trichloro-2-hydroxy-diphenyl ether. Such antimicrobial agents when used in amounts up to about 0.5% by weight inhibit bacterial action present in perspiration, thereby reducing the resultant unpleasant odors. Other examples include perfumes, present in amounts up to about 0.8% by weight.

The following examples further illustrate the improved effectiveness and the preferred embodiments of the present invention. Such examples shall not be construed to be limiting. Variations of the present invention will be readily apparent to those skilled in the art.

In addition to the following examples, other suitable compositions into which the present invention can be embodied are found in U.S. Pat. Nos. 2,236,387; 3,288,681; and 2,045,152; British Pat. No. 987,301; and Netherlands application 66/13943. Such references are incorporated in and made part of this application by reference.

EXAMPLE I 1600 grams of diisopropyl adipate, the emollient-carrier liquid, and 120 grams of stearoyl monoethanol amide, the suspending agent, were weighed into a vessel and heated to about 160° F., whereupon the mixture was completely liquefied. 700 grams of aluminum chlorhydroxide (17% moisture powder), the antiperspirant compound, was added and the resulting concentrate was mixed for 5 minutes. As it cooled to about 100° F. the sides of the vessel were scraped occasionally by hand. The concentrate was allowed to stand for about 5 hours during which time it formed a solid gel. This gel was whipped with an agitator until it became fluid. 20 grams of trichlorocarbanilide were then added and mixed in. Perfume was then added. Portions of the batch were transferred to aerosol containers which were then sealed and pressure filled with propellant to yield the following composition:

| Component | % by Weight |
|---|---|
| Aluminum chlorhydroxide | 3.5 |
| Stearoyl monoethanol amide | 0.6 |
| Diisopropyl adipate | 8.0 |
| Trichlorocarbanilide | 0.1 |
| Perfume | 0.3 |
| Propellant-$CCl_3F$:$CCl_2F_2$::60/40 | 87.5 |
| (weight ratio) | 100.0 |

The result was a powder aerosol composition having improved antiperspirant efficacy and possessing desirable cosmetic qualities.

The same process is used to prepare compositions identical to the foregoing except that diisopropyl adipate is substitute by ethyl ethylcarbomethyl phthalate, diethyl sebacate, and di-n-butyl phthalate,respectively. Antiperspirant effectiveness and general cosmetic properties substantially equivalent to the foregoing are obtained in that the antiperspirant effectiveness is better than that obtainable with generally recognized prior art emollients such as isopropyl myristate.

EXAMPLE II

Forty-eight pounds of ethyl ethylcarbomethyl phthalate and 3.6 lb. of coconut monoethanol amide are weighed into a drum and heated to about 160° F., whereupon the mixture is completely liquefied. Twenty-one pounds of aluminum chlorhydroxide are added and the resulting concentrate is mixed for 5 minutes. The mixture is cooled to about 120° F. with agitation and allowed to stand overnight. Five and seven-tenths pounds perfume and 0.6 lb. trichlorocarbanilide is added and mixed in. The batch is packed into aerosol containers by adding 21 gm. of the above concentrate; sealing; and pressure filling with 143 gm. of a 60/40 mixture of $CCl_3F/CCl_2F_2$. The composition is:

| Component | % by Weight |
|---|---|
| Aluminum chlorhydroxide | 3.5 |
| Coconut monoethanol amide | 0.6 |
| Diisopropyl adipate | 8.0 |
| Trichlorocarbanilide | 0.1 |
| Perfume | 0.4 |
| Propellant-$CCl_3F:CCl_2F_2$::60/40 | 87.4 |
| (weight ratio) | 100.0 |

Antiperspirant properties are good and general cosmetic properties are good.

The same process is used to prepare compositions identical to the above except that the aluminum chlorhydroxide is replaced by other antiperspirant salts: aluminum chloride, aluminum sulfate, aluminum oxychloride, aluminum oxysulfate, zirconyl hydroxychloride, zirconium oxychloride, zinc sulfate, and zinc sulfocarbolate. Also used are complexes of zirconium salt/amine/amino acid, zirconium salt/aluminum hydroxychloride/glycol, aluminum hydroxychloride/glycol, zirconyl hydroxychloride/aluminum hydroxychloride complex of Example I of the copending Bolich application referred to hereinbefore, and aluminum hydroxychloride/zirconyl hydroxychloride/glycine complex of the copending Leudders application referred to hereinbefore. Good antiperspirant properties are exhibited and general physical properties are substantially the same as those of the above.

EXAMPLE III

Forty grams of diethyl sebacate and 3 gm. octadecyl monoethanol amideare heated to 190° F. and mixed; then cooled to 180° F. and 17.5 grams of aluminum chlorhydroxide and 0.5 gm. trichlorocarbanilide are added and mixed while natural cooling is allowed to occur. Perfume in the amount of 2.2 gm. is added when the mix reaches 150° F. The batch is chilled for 20–30 minutes and remixed; then added to aerosol containers to which 262.1 gm. $CCl_3F$ is added by pressure fill. The composition has good general cosmetic properties and good antiperspirant effectiveness.

The same process is used to prepare compositions identical to the foregoing except that the propellant of Example III is replaced with 1,1-difluoroethane, 1-chloro-1,1-difluoroethane, dichloromonofluoromethane, methylene chloride, methyl chloroform, vinyl fluoride, vinylidene fluoride, trichlorofluoromethane, dichlorodifluoromethane, dichlorotetrafluoroethane, monochlorodifluoromethane, trichlorotrifluoroethane, propane, butane, and isobutane, alone and mixtures thereof. In each case, the general cosmetic properties and the antiperspirant effectiveness of the composition when applied to the skin are substantially the same as that discussed above.

EXAMPLE IV

Forty-two grams of aluminum chlorhydroxide, 3.6 gm tetradecyl amine, 48 gm. diisopropyl adipate, and 0.6 gm. trichlorocarbanilide are weighed into a vessel, heated to about 180° F. and allowed to cool to 100° F. Two and four-tenths grams of perfume is added and the batch mixed again. Portions of the concentrate are transferred to aerosol containers which are then sealed and filled with propellant by the method of Example III to yield the following composition:

| Component | % by Weight |
|---|---|
| Aluminum chlorhydroxide | 7.0 |
| Bentone 38 | 0.6 |
| Diisopropyl adipate | 8.0 |
| Trichlorocarbanilide | 0.1 |
| Perfume | 0.4 |
| Propellant-$CCl_3F:CCl_2F_2$::60/40 | 83.9 |
| (weight ratio) | 100.0 |

Antiperspirant properties are good and general cosmetic properties are good.

The same process is used to prepare compositions identical to the foregoing except that Bentone 38 is replaced by Cab-O-Sil M-5, coconut monoethanol amide, octadecyl monoethanol amide, stearoyl monoethanol amide, lauryl amine, stearyl amine, tetradecyl amine, hexadecyl amine, octadecyl, amine and eicosyl amine, respectively. The result is powder antiperspirant compositions having antiperspirant and cosmetic properties substantially equivalent to the foregoing.

The same process is used to prepare compositions identical to the above except that the trichlorocarbanilide is replaced by an equivalent amount of hexachlorophene, trifluoromethylcarbanilide, tribromosalicylanilide, and 2,4,4'-trichloro-2-hydroxy-diphenyl ether.

In each case, the general cosmetic properties and the antiperspirant effectiveness of the composition when applied to the skin are substantially the same as that discussed above.

The same process is used to prepare compositions identical to the foregoing except that the antimicrobial and perfume are left out. The cosmetic and antiperspirant properties are substantially the same as that described above.

EXAMPLE V

Compositions are prepared having the following formulations:

| Component | % by Weight | | | |
|---|---|---|---|---|
| | a | b | c | d |
| Aluminum chlorhydroxide | 4.0 | 2.0 | 5.0 | 12.0 |
| Bentone 38 | 0.1 | 0.2 | 0.5 | 1.0 |
| Diisopropyl adipate | 1.0 | 6.0 | 10.0 | 15.0 |
| Trichlorocarbanilide | 0.5 | 0.1 | 0.3 | 0.5 |

-continued

| Component | % by Weight | | | |
|---|---|---|---|---|
| | a | b | c | d |
| Perfume | 0.5 | 0.4 | 0.6 | 0.8 |
| Propellant CCl₃F:CCl₂F₂: 60/40 (weight ratio) | 93.9 | 91.3 | 83.6 | 70.7 |
| | 100.0 | 100.0 | 100.0 | 100.0 |

General physical properties and antiperspirant effectiveness of each formulation are good.

Compositions identical to those prepared in Example V — a, b, c and d above are prepared except that in each case the aluminum chlorhydroxide is replaced by an equivalent amount of aluminum chloride, aluminum sulfate, aluminum oxychloride, aluminum oxysulfate, zirconyl hydroxychloride, zirconium oxychloride, zinc sulfate zinc sulfocarbolate, complexes of zirconium salt/amine/amino acid, zirconium salt/aluminum hydroxychloride/glycol, aluminum hydroxychloride/glycol, the aluminum-zirconium complexes disclosed in the copending Bolich application, Ser. No. 59,690 filed July 30, 1970 heretofore incorporated herein by reference, and the aluminum and zirconium hydroxychloride complexes as disclosed in the copending Luedders application Ser. No. 130,833 filed Apr. 2, 1971 referred to hereinbefore.

Good physical and antiperspirant properties are attained in each case.

Identical compositions to those of Example V are prepared, except that, each case, the Bentone-38 is replaced by an equivalent amount of Cab-O-Sil M-5, coconut monoethanol amide, octadecyl monoethanol amide, stearoyl monoethanol aide, lauryl amine, stearyl amine, tetradecyl amine, hexadecyl amine, octadecyl amine and eicosyl amine. In each instance, an antiperspirant composition having desirable physical and antiperspirant properties results.

Compositions identical to those of Example V are prepared, except that the diisopropyl adipate is replaced by equivalent amounts of di-n-butyl phthalate, diethyl sebacate, and ethyl ethylcarbomethyl phthalate [ortho C₂H₅OOC-φ-COOCH₂COOC₂H₅]. In each instance, an antiperspirant composition results having highly desirable physical properties and antiperspirant effectiveness.

Identical compositions to those of Example V are prepared, except that the trichlorocarbanilide is replaced by equivalent amounts of hexachlorophene, trifluoromethylcarbanilide, tribromosalicylanilide, 2,4,4'-trichloro-2-hydroxy-diphenyl ether and mixtures thereof.

The resulting compositions possess good general physical properties and antiperspirant effectiveness.

Compositions of the formulas prepared in Example V are prepared, except the propellant mixture utilized in the compositions is replaced by, in each instance, equivalent amounts of 1,1-difluoroethane, 1-chloro -1,1-difluoroethane, dichloromonofluoromethane methylene chloride, methyl chloroform, vinyl fluoride, vinylidene fluoride, trichlorofluoromethane, dichlorodifluoromethane, dichlorotetrafluoroethane, monochlorodifluoromethane, trichlorotrifluoroethane, propane, butane, and isobutane,, alone and mixtures thereof. In each case, general cosmetic properties and antiperspirant effectiveness are desirable.

What is claimed is:

1. A powder aerosol antiperspirant composition consisting essentially of:
   A. from about 1.0% to about 12% by weight of a finely divided powder antiperspirant compound that is insoluble in the composition, said compound being based on salts selected from the group consisting of aluminum chlorhydroxide, aluminum chloride, aluminum sulfate, aluminum oxychloride, aluminum oxysulfate, zirconyl hydroxychloride zirconium oxychloride, zinc sulfate and zinc sulfocarbolate;
   B. from about 0.1% to about 1% by weight of a suspending agent for the antiperspirant compound, which suspending agent is a hydrophobic clay that swells in organic solvents;
   C. from about 1.0% to about 15% by weight of a hydrophobic emollient-carrier liquid which is a multiple ester of an organic acid wherein said ester contains from about 12 to about 16 carbon atoms, and said ester has a ratio of ester groups to carbon atoms of from about 0.125 to about 0.214 and wherein said ester has a solubility in water of from about 0.0005% to about 0.1% at 30° C.; and
   D. from about 70.7% to about 93.9% of anhydrous liquefiable propellant gas under pressure to produce an aerosol spray.

2. The composition of claim 1 wherein component (C) is selected from the group consisting of di-n-butyl phthalate, diethyl sebacate, ethyl ethylcarbomethyl phthalate and diisopropyl adipate.

3. The composition of claim 2 wherein component (C) is diisopropyl adipate.

4. The composition of claim 1 wherein component (C) comprises from about 6% to about 10% by weight of the composition.

5. The composition of claim 1 wherein the powder antiperspirant is selected from the group consisting of aluminum chlorhydroxide, and complexes of aluminum chlorhydroxide and zirconyl hydroxychloride.

6. The composition of claim 1 wherein the powder antiperspirant is a complex of aluminum chlorhydroxide/zirconyl hydroxychloride/amino acid.

7. The composition of claim 1 wherein the powder antiperspirant is aluminum chlorhydroxide. stearyl amine, tetradecyl amine, hexadecyl amine, octadecyl amine, and eicosyl amine.

8. The composition of claim 1 wherein the propellant gas is selected from the group consisting of trichlorofluoromethane, dichlorodifuoromethane, dichlorotetrafluoroethane, monochlorodifuoromethane, trichlorotrifluoroethane, propane, butane, 1,1-difluoroethane, 1,1-difluoro-1-chloroethane, dichloromonofluoromethane, methylene chloride, and mixtures thereof.

* * * * *